United States Patent [19]
Toki

[11] Patent Number: 5,386,452
[45] Date of Patent: * Jan. 31, 1995

[54] METHOD AND APPARATUS FOR HELICAL SCAN IMAGING IN X-RAY COMPUTED TOMOGRAPHY

[75] Inventor: Yusuke Toki, Utsunomiya, Japan

[73] Assignee: Kabushiki Kaisha Toshiba, Kanagawa, Japan

[*] Notice: The portion of the term of this patent subsequent to Jun. 29, 2010 has been disclaimed.

[21] Appl. No.: 64,936

[22] Filed: May 24, 1993

Related U.S. Application Data

[63] Continuation of Ser. No. 784,223, Oct. 30, 1991, Pat. No. 5,224,135.

[30] Foreign Application Priority Data

Nov. 1, 1990 [JP] Japan ................... 2-293595

[51] Int. Cl.$^6$ ............................. A61B 6/03
[52] U.S. Cl. ......................... 378/146; 378/4; 378/15
[58] Field of Search ............. 378/4, 146, 15, 20, 378/62, 68, 205, 193, 195

[56] References Cited

U.S. PATENT DOCUMENTS

| | | | |
|---|---|---|---|
| 4,789,929 | 12/1988 | Nishimura et al. | 378/20 |
| 5,212,717 | 5/1993 | Hada | 378/146 |
| 5,224,135 | 6/1993 | Toki | 378/4 |

FOREIGN PATENT DOCUMENTS

| | | |
|---|---|---|
| 0113879A3 | 7/1984 | European Pat. Off. . |
| 0383232A2 | 8/1990 | European Pat. Off. . |
| 0450152A1 | 10/1991 | European Pat. Off. . |

Primary Examiner—David P. Porta
Assistant Examiner—Don Wong
Attorney, Agent, or Firm—Finnegan, Henderson, Farabow, Garrett & Dunner

[57] ABSTRACT

A method and an apparatus for a helical scan imaging in an X-ray CT, in which the initial set up operation can be achieved easily and accurately. In this X-ray CT apparatus, a relative linear motion of the bed plate and the X-ray source is automatically controlled according to the desired imaging region specified by the operator such that the bed plate and the X-ray source is relatively linearly moved through a distance covered by a scanning region appropriate for collecting the data required in order to reconstruct the tomographic images for the desired imaging region. The scanning region includes the desired imaging region and the supplementary interpolation data regions, located at ends of the desired imaging region and utilized in carrying out interpolations for deriving data in the desired imaging region; an initial acceleration region for accounting an initial acceleration of the bed plate; and a final deceleration region for accounting a final deceleration of the bed plate.

20 Claims, 4 Drawing Sheets

METHOD AND APPARATUS FOR HELICAL SCAN IMAGING IN X-RAY COMPUTED TOMOGRAPHY

This is a continuation of application Ser. No. 07/784,223, filed Oct. 30, 1991, now U.S. Pat. No. 5,224,135.

BACKGROUND OF THE INVENTION

1. Field of the Invention

The present invention relates to an X-ray computed tomography (CT), and more particularly to a so called helical scan imaging in which a body to be examined is moved along its body axis during the scanning operation in such an X-ray CT.

2. Description of the Background Art

Recently, there has been a proposition of an X-ray CT apparatus capable of carrying out a so called helical scan imaging. As shown in FIG. 1, in the helical scan imaging, a body to be examined P located on a bed plate 100 is moved along a direction of its body axis while an X-ray tube 101 and a detector 102 is rotated around the body to be examined P, such that the X-ray tube 101 moves along a helical trajectory 103 shown in FIG. 2 relative to the body to be examined P. In reconstructing the image from the data collected by such a helical scan, tomographic image data are obtained from data collected during one rotation around the body P to be examined, such as those collected between points a and b shown in FIG. 2. Such a helical scan imaging has an advantage that the three-dimensional information on the body P to be examined can be obtained in a relatively short period of time.

Now, in such a helical scan imaging, the slice plane obtained from data collected between the points a and b does not appear like a normal slice plane shown in FIG. 3A which can be obtained by ordinary scans, but appears as shown in FIG. 3B in which 0° plane and 360° plane do not coincide with each other. Hence, when these data are directly used in reconstructing the image, the strong artefacts appear on the reconstructed image. For this reason, the reduction of the artefacts is achieved by deriving the data of the same single slice plane from the collected data by using the interpolation as follows.

For example, as shown in FIG. 4, the data at a point C of a desired rotational phase on a desired slice plane can be obtained by using the interpolation of the data $d_A$ of the point A in the same rotational phase as that of the point C and on a part of the trajectory 103 neighboring the point C, and the data $d_B$ of the point B in the same rotational phase as that of the point C and on another part of the trajectory 103 neighboring the point C. Therefore, in a case of using a linear interpolation, the data $d_C$ at the point C can be obtained by the following expression:

$$d_C = \frac{m}{l + m} \times d_A + \frac{l}{l + m} \times d_B$$

where l is a distance between the points A and C, and m is a distance between the points B and C, as shown in FIG. 4.

Now, as shown in FIG. 5, in reconstructing the image from the data collected by the helical scan, in order to obtain the necessary data for reconstructing the image at a slice center position E, the data must be collected at least at a main data region D which covers a half rotation (180°) ahead and a half rotation (180°) behind the slice center position E in a case of a full scan.

In addition, in the case whose data for reconstruction are to be derived from the collected data by using the interpolation, the data must also be collected at supplementary data regions F and G which cover a half rotation (180°) ahead and a half rotation (180°) behind the main data region D. Namely, in order to obtain the data at a point C' on the slice center position E by the interpolation, the data at a point A' in the main data region D as well as the data at a point B' in the supplementary data region F become necessary. Also, in order to obtain the data at a point C" on the slice center position E by the interpolation, the data at a point A" in the main data region D as well as the data at a point B" in the supplementary data region G become necessary.

Therefore, the operator must position the body to be examined P and the bed plate 100 and set up the scanning region such that the scan and the data collection can be carried out for the main data region D and possibly also for the supplementary data regions F and G if necessary, according to the desired imaging regions on the body to be examined P.

Moreover, it is further preferable for the operator to position the body to be examined P and the bed plate 100 and set up the scanning region such that the scan also covers the regions for the initial acceleration and the final deceleration of the motion of the bed plate 100 along the body axis of the body to be examined P at which the data collection is unnecessary, so as to obtain the accurate data collected only while the bed plate 100 is moving at a constant speed.

However, in a conventional X-ray CT apparatus capable of carrying out the helical scan imaging, the operator must carry out the initial set up operation including the positioning of the body to be examined P and the bed plate 100 and setting up of the scanning region described above, on his own discretion. Hence, these positioning and setting up operations are cumbersome and not very accurate.

SUMMARY OF THE INVENTION

It is therefore an object of the present inventor to provide a method and an apparatus for helical scan imaging in an X-ray CT, in which the initial set up operation can be achieved easily and accurately, without relying heavily on the discretion of the operator.

According to one aspect of the present invention an X-ray CT apparatus is provided for carrying out a helical scan imaging, comprising: input means for entering a desired imaging region; a bed plate for carrying a body to be examined along a direction of the body axis of the body to be examined, which is linearly movable along the direction of the body axis of the body to be examined; an X-ray tube for irradiating X-rays on the body to be examined on the bed plate; a detector for detecting the X-rays irradiated by the X-ray tube and penetrated through the body to be examined, where the X-ray tube and the detector are integrally rotatable around the body to be examined at a predetermined constant angular speed; data collection means for collecting data concerning the X-rays detected by the detector according to the desired imaging region entered by the input means; image reconstruction means for reconstructing tomographic images according to the data collected by the data collection means; and bed plate control means for controlling a linear motion of the bed plate according to the desired imaging region entered by the input means such that the bed plate is linearly moved through a distance covered by a scanning region appropriate for the data collection means to collect the data required by the image reconstruction means to reconstruct the tomographic images for the desired imaging region.

According to another aspect of the present invention a method of a helical scan imaging in an X-ray CT is provided, comprising the steps of: placing a body to be examined on a bed plate which is linearly movable along a direction of a body axis of the body to be examined; entering a desired imaging region; integrally rotating an X-ray tube for irradiating X-rays on the body to be examined on the bed plate and a detector for detecting the X-rays irradiated by the X-ray tube and penetrated through the body to be examined, around the body to be examined at a predetermined constant angular speed; collecting data concerning the X-rays detected by the detector according to the desired imaging region entered at the entering step; reconstructing tomographic images according to the data collected at the collecting step; and automatically controlling a linear motion of the bed plate according to the desired imaging region entered at the entering step such that the bed plate is linearly moved through a distance covered by a scanning region appropriate for the collecting step to collect the data required by the reconstructing step to reconstruct the tomographic images for the desired imaging region.

Other features and advantages of the present invention will become apparent from the following description taken in conjunction with the accompanying drawings.

DETAILED DESCRIPTION OF THE PREFERRED EMBODIMENTS

Figure 1:
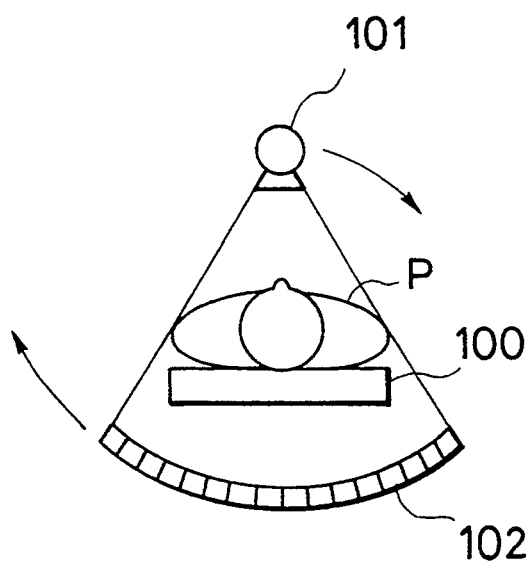
FIG. 1 is a front view of a main part of a conventional X-ray CT apparatus for carrying out a helical scan imaging.
Figure 2:
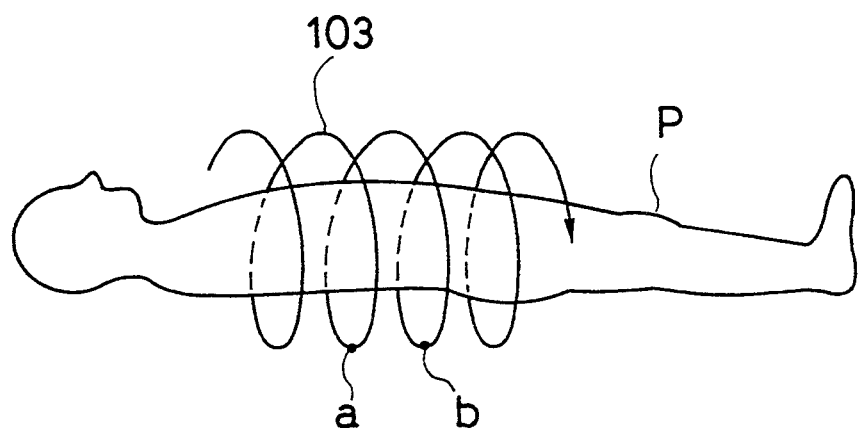
FIG. 2 is a perspective view of a body to be examined, showing a trajectory of an X-ray tube around the body to be examined realizing in the helical scan imaging.
Figure 3A:
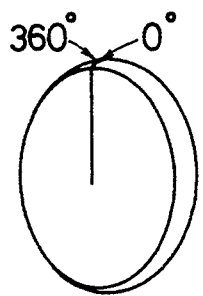
FIG. 3A is a perspective view of a typical slice plane obtained by an ordinary scanning in an X-ray CT apparatus.
Figure 3B:
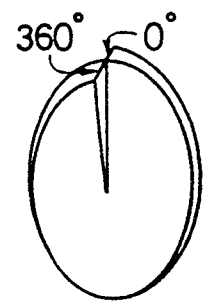
FIG. 3B is a perspective view of a typical slice plane obtained by the helical scan imaging in an X-ray CT apparatus.
Figure 4:
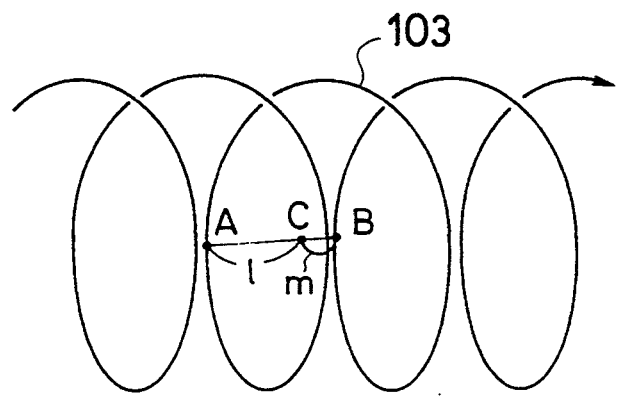
FIG. 4 is a perspective view of a trajectory of the X-ray tube realizing in the helical scan imaging, for explaining the linear interpolation and deriving the data for the image reconstruction.
Figure 5:
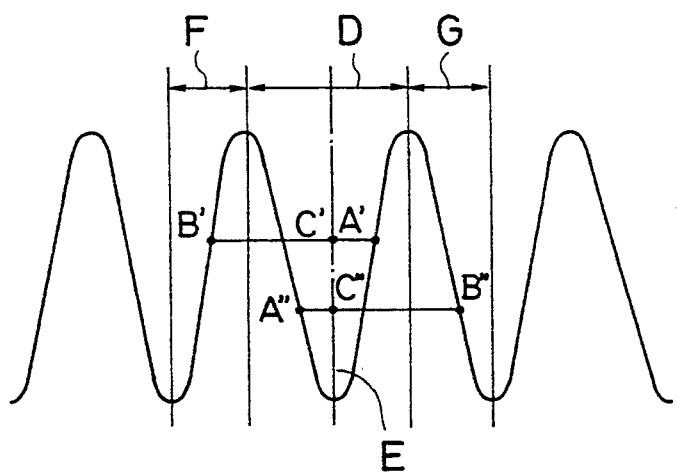
FIG. 5 is a side view of a trajectory of the X-ray tube realizing in the helical scan imaging, for explaining a main data region and supplementary data regions to be set up around a slice center position.
Figure 6:
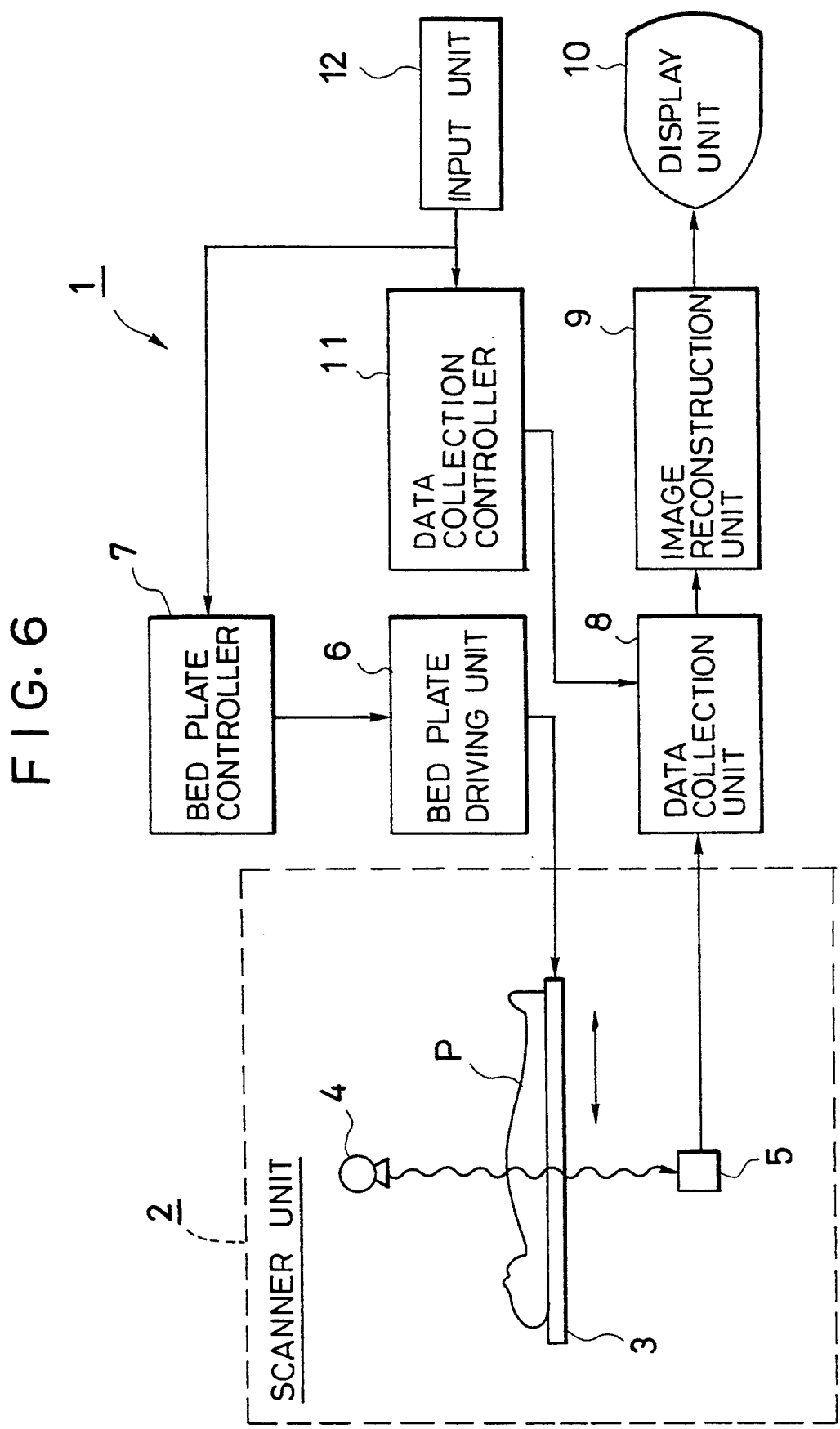
FIG. 6 is a schematic block diagram of one embodiment of an X-ray CT apparatus according to the present invention.

Referring now to FIG. 6, one embodiment of an X-ray CT apparatus according to the present invention will be described in detail.

In this embodiment, an X-ray CT apparatus 1 has a scanner unit 2 for scanning with respect to a body P to be examined, including a bed plate 3 for carrying the body P to be examined along a direction of the body axis of the body to be examined P, an X-ray tube 4 for irradiating X-rays on the body to be examined P on the bed plate 3, and a detector 5 for detecting the X-rays irradiated by the X-ray tube 4 and penetrated through the body to be examined P, where the bed plate 3 is linearly movable along the direction of the body axis of the body to be examined P, while the X-ray tube 4 and the detector 5 are integrally rotatable around the body to be examined P at a predetermined constant angular speed. In this scanner unit 2, the helical scan imaging is carried out by moving the body to be examined P located on the bed plate 3 along the direction of the body axis of the body to be examined P while rotating the X-ray tube 4 and the detector 5 around the body to be examined P, such that the X-ray tube 4 moves along a helical trajectory relative to the body to be examined P.

In addition, this X-ray CT apparatus 1 further comprises a bed plate driving unit 6 for driving the bed plate 3 in the linear motion along the direction of the body axis of the body to be examined P; a bed plate controller 7 for controlling the driving operation by the bed plate driving unit 6 in order to control the linear motion of the bed plate 3 appropriately; a data collection unit 8 for collecting data from the X-rays detected by the detector 5; an image reconstruction unit 9 for reconstructing the tomographic images according to the data collected by the data collection unit 8; a display unit 10 for displaying the tomographic images reconstructed by the image reconstruction unit 9; a data collection controller 11 for controlling the data collection operation of the data collection unit 8 appropriately; and the input unit 12 from which an operator enters a desired scanning region, according to which the bed plate controller 7 and the data collection controller 11 control the bed plate driving unit 6 and the data collection unit 8.

In carrying out the helical scan imaging in this X-ray CT apparatus, the operator enters the desired imaging region in which the tomographic images are to be obtained for the slice planes located therein, through the input unit 12, and places the body to be examined P on the bed plate 3 such that a scan start side end of the imaging region is located at a predetermined scanning position.

Then, in accordance with the desired imaging region entered at the input unit 12, the bed plate controller 7 and the data collection controller 11 controls the bed plate driving unit 6 and the data collection unit 8 as follows.

Figure 7:
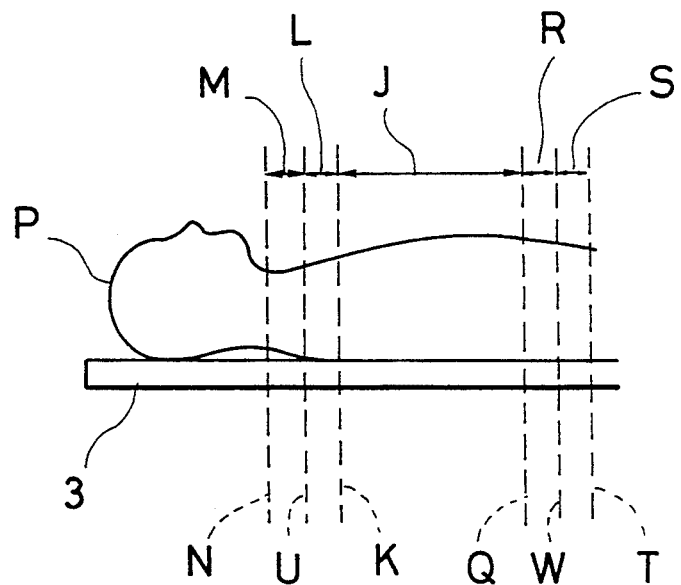
FIG. 7 is a side view of a body to be examined, showing one possible initial set up realizable in the apparatus of FIG. 6.

As shown in FIG. 7, when the imaging region J is set up with respect to the body to be examined P with a scan start side end K located at the scanning position, the bed plate controller 7 automatically determines extra data regions L and R. Each of regions L and R includes a half main data region covering a half rotation (180°) part of a main data region for a first slice plane in the imaging region J and an associated supplementary data region covering additional half rotation (180°) adjacent to the half main data region, as well as an initial acceleration region M for accounting an initial acceleration of the bed plate 3 and a final deceleration region S for accounting a final deceleration of the bed plate 3. The bed plate controller 7 controls the bed plate driving unit 6 to move the bed plate 3 in a direction opposite to a scanning direction for a predetermined distance such that a scan start side end N of the initial acceleration region M is moved to the scanning position.

Here, the extra data regions L and R, the initial acceleration region M, and the final deceleration region S can be determined in advance according to the predetermined constant rotational speed of the X-ray tube 4 and the detector 5 and a linear motion characteristic of the bed plate 3.

Then, as the helical scan imaging starts, the X-ray tube 4 and the detector 5 are integrally rotated at a predetermined constant angular speed around the body to be examined P at the scanning position while the bed plate controller 7 controls the bed plate driving unit 6 to move the bed plate 3 in the scanning direction such that the scanning is carried out for the entire scanning region formed by the imaging region J, extra data regions L and R, initial acceleration region M, and final deceleration region S. This is done until a scan finish side end T of the final deceleration region S stops at the scanning position.

As a result, the bed plate 3 initially accelerates for a distance covered by the initial acceleration region M, moves at a predetermined constant linear speed through a distance covered by the extra data regions L and R and the imaging region J, and finally decelerates for a distance covered by the final deceleration region S, such that the X-ray tube 4 moves along a helical trajectory relative to the body to be examined P.

Meanwhile, when the imaging region J is set up with respect to the body to be examined P with a scan start side end K located at the scanning position, the data collection controller 11 also similarly determines extra data regions L and R as well as the initial acceleration and the final deceleration region S around the imaging region J automatically. The data collection controller 11 controls the data collection unit 8 such that the data from the X-rays detected by the detector 5 are collected only in the extra data regions L and R and the imaging region J. In other words, the data are collected by the data collection unit 8 between a scan start side end U of the extra data region L and a scan finish side end W of the extra data region R.

Then, the data collected by the data collection unit 8 from the extra data regions L and R and the imaging region J are fed to the image reconstruction unit 9 in which image data necessary to reconstruct the tomographic images at desired slice planes are derived by using the interpolation on the collected data, and the tomographic images at the desired slice planes are reconstructed by using the derived image data. Here, the interpolation can be achieved similarly to a conventional manner described above in the background of the invention section. The reconstructed tomographic images are then displayed on the display unit 10.

Thus, according to this embodiment, the initial set up operation for the helical scan imaging can be achieved by simply specifying the desired imaging region J at the input unit 12, so that the scanning region can be set up accurately, while reducing the burden of the operator.

It is to be noted that in a case where the imaging region J is too wide to be covered by a single scan such that more than one scans are required, the bed plate controller 7 may control the bed plate driving unit 6 as follows.

Figure 8:
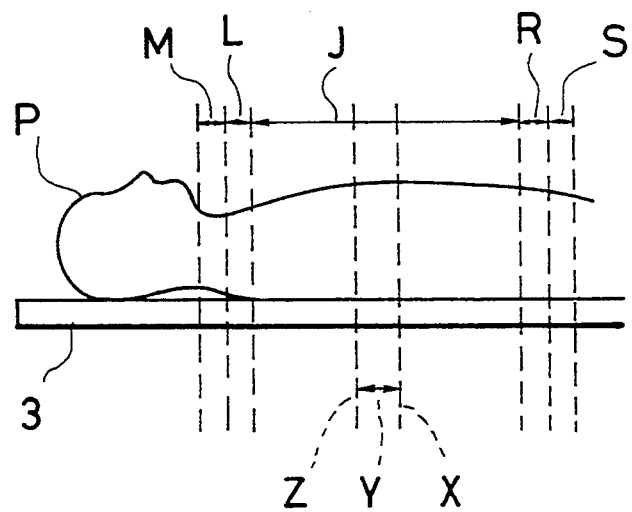
FIG. 8 is a side view of a body to be examined, showing another possible initial set up realizable in the apparatus of FIG. 6.

In such a case, as shown in FIG. 8, when the first scan finishes at a position X, the bed plate controller 7 determines a readjustment region Y containing another extra data region adjacent to the position X, correction data region, and another initial acceleration region, and controls the bed plate driving unit 6 to move the bed plate 3 in a direction opposite to a scanning direction for such a distance that a scan start side end Z of the readjustment region Y is moved to the scanning position. Hence, the next scan can be started at the scan start side end Z of the readjustment region Y.

Here, the correction data region is provided in the readjustment region Y in order to obtain additional data necessary in removing the inconsistency in the collected data due to the displacement of the slice plane caused by the physical motion of the body to be examined P during the readjustment between the successive scans. Thus, in this case, the data collected at the additional extra region and the correction data region overlap with the data collected in the previous scan, so as to enable the effective data correction for the subsequent scan. Furthermore, the readjustment may be achieved such that the data collected at a part of the main data region in the subsequent scan also overlap with the data collected in the previous scan, in order to account for the physical motion of the target portion of the body to be examined P due to breathing or some other cause during the readjustment between the successive scans.

It is also to be noted that, in the above embodiment, any one of the initial acceleration region M, final deceleration region S, and a supplementary data region in the the extra data regions L and R may be omitted if its omission is preferred.

Moreover, although the above embodiment has been described for a third generation type X-ray CT apparatus, the present invention is equally applicable to a fourth generation type X-ray CT apparatus.

Similarly, although the above embodiment has been described for a case of a full scan using a full 360° rotation of the X-ray tube and a detector around the body to be examined, the present invention is also equally applicable to an X-ray CT apparatus for carrying out a half scan in which the data for one rotation are obtained by using scans of 90° plus a fan angle on both sides of the desired image center position.

Besides these, many modifications and variations the above embodiment may be made without departing from the novel and advantageous features of the present invention. Accordingly, all such modifications and variations are intended to be included within the scope of the appended claims.

What is claimed is:

1. An X-ray computed tomography (CT) apparatus for carrying out a helical scan imaging, comprising:
   input means for entering a desired imaging region, the desired imaging region having slice planes located at ends of the desired imaging region;
   a bed plate for supporting a body, including a body axis, to be examined along a direction of said body axis;
   an X-ray source for irradiating X-rays on the body to be examined on the bed plate, the X-ray source and the bed plate being relatively rotatable with respect to each other at a predetermined angular speed and relatively linearly movable with respect to each other along the direction of the body axis of the body to be examined;

a detector for detecting the X-rays irradiated by the X-ray source and penetrated through the body to be examined;

data collection means for collecting data from the X-rays detected by the detector according to the desired imaging region entered by the input means;

image reconstruction means for reconstructing tomographic images according to the data collected by the data collection means; and control means for controlling a relative linear motion of the X-ray source and the bed plate according to the desired imaging region entered by the input means such that the X-ray source and the bed plate are relatively linearly moved through a distance covered by a scanning region appropriate for the data collection means to collect the data required by the image reconstruction means to reconstruct the tomographic images for the desired imaging region, the scanning region including the desired imaging region and supplementary interpolation data regions, each of the supplementary interpolation data regions being located at the ends of the desired imaging region and utilized in carrying out interpolations for deriving data in the desired imaging region.

2. The X-ray CT apparatus of claim 1, wherein each of the supplementary interpolation data regions corresponds to 180° rotation of the X-ray source around the body to be examined.

3. The X-ray CT apparatus of claim 1, wherein the data collection means collects the data from the desired imaging region and the supplementary interpolation data regions.

4. The X-ray CT apparatus of claim 1, wherein the scanning region includes an initial acceleration region for accounting an initial relative acceleration of the bed plate and the X-ray source with respect to each other.

5. The X-ray CT apparatus of claim 1, wherein the scanning region includes a final deceleration region for accounting a final relative deceleration of the bed plate and the X-ray source with respect to each other.

6. The X-ray CT apparatus of claim 1, wherein the scanning region is determined in advance according to the predetermined angular speed of the relative rotation of the X-ray source and the bed plate and a linear motion characteristic of the relative linear motion of the X-ray source and the bed plate.

7. The X-ray CT apparatus of claim 1, wherein the control means controls the bed plate and the X-ray source to relatively move the distance covered by the scanning region in a plurality of scans, the relative linear motion of the bed plate and the X-ray source being controlled such that each scan by the bed plate and the X-ray source includes a readjustment region which overlaps with a region covered by a previous scan.

8. The X-ray CT apparatus of claim 7, wherein the readjustment region includes a correction data region from which additional data necessary in removing inconsistency in the data collected by the data collection means introduced by a readjustment between the successive scans are collected by the data collection means.

9. The X-ray CT apparatus of claim 1, wherein the X-ray source carries out a full scan using a full 360° rotation around the body to be examined.

10. The X-ray CT apparatus of claim 1, wherein the bed plate is linearly movable along the direction of the body axis of the body to be examined, while the X-ray source is rotatable around the body to be examined at the predetermined angular speed.

11. A method of a helical scan imaging in an X-ray computed tomography (CT), comprising the steps of:

placing a body to be examined on a bed plate;

entering a desired imaging region, the desired imaging region having slice planes located at ends of the desired imaging region;

relatively linearly moving the bed plate and an X-ray source for irradiating X-rays on the body to be examined with respect to each other along a direction of a body axis of the body to be examined, while relatively rotating the bed plate and the X-ray source with respect to each other at a predetermined angular speed;

detecting the X-rays irradiated by the X-ray source and penetrated through the body to be examined by a detector;

collecting data from the X-rays detected by the detector according to the desired imaging region entered at the entering step;

reconstructing tomographic images according to the data collected at the collecting step; and automatically controlling a relative linear motion of the bed plate and the X-ray source according to the desired imaging region entered at the entering step such that the X-ray source and the bed plate is relatively linearly moved through a distance covered by a scanning region appropriate for the collecting step to collect the data required by the reconstructing step to reconstruct the tomographic images for the desired imaging region, the scanning region including the desired imaging region and supplementary interpolation data regions, each of the supplementary interpolation data regions being located at the ends of the desired imaging region and utilized in carrying out interpolations for deriving data in the desired imaging region.

12. The method of claim 11, wherein each of the supplementary interpolation data regions corresponds to 180° rotation of the X-ray source around the body to be examined.

13. The method of claim 11, wherein the collecting step includes collecting the data from the desired imaging region and the supplementary interpolation data regions.

14. The method of claim 11, wherein the scanning region includes an initial acceleration region for accounting an initial relative acceleration of the bed plate and the X-ray source with respect to each other.

15. The method of claim 11, wherein the scanning region includes a final deceleration region for accounting a final relative deceleration of the bed plate and the X-ray source with respect to each other.

16. The method of claim 11, wherein said controlling step includes determining the scanning region in advance according to the predetermined angular speed of the relative rotation of the bed plate and the X-ray source and a linear motion characteristic of the relative linear motion of bed plate and the X-ray source.

17. The method of claim 11, wherein the controlling step includes controlling the bed plate and the X-ray source to relatively move the distance covered by the scanning region in a plurality of scans, and controlling the relative linear motion of the bed plate and the X-ray source such that each scan by the bed plate and the X-ray source includes a readjustment region which overlaps with a region covered by a previous scan.

18. The method of claim 17, wherein the readjustment region includes a correction data region from which additional data necessary in removing inconsistency in the data collected at the collecting step introduced by a readjustment between the successive scans are collected at the collecting step.

19. The method of claim 11, wherein the relatively linearly moving step includes rotating the X-ray source in a full scan using a full 360° rotation around the body to be examined.

20. The method of claim 11, wherein the relatively linearly moving step includes linearly moving the bed plate along the direction of the body axis of the body to be examined and rotating the X-ray source around the body to be examined at the predetermined angular speed.

* * * * *